(12) United States Patent
Bruhn et al.

(10) Patent No.: US 11,048,715 B1
(45) Date of Patent: *Jun. 29, 2021

(54) AUTOMATED FILE ACQUISITION, IDENTIFICATION, EXTRACTION AND TRANSFORMATION

(71) Applicant: Open Invention Network, LLC, Durham, NC (US)

(72) Inventors: David M. Bruhn, Moorpark, CA (US); Douglas L. Capitano, Berthoud, CO (US)

(73) Assignee: Open Invention Network, LLC, Durham, NC (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/431,253

(22) Filed: Jun. 4, 2019

Related U.S. Application Data

(63) Continuation of application No. 15/335,028, filed on Oct. 26, 2016, now Pat. No. 10,311,076.

(51) Int. Cl.
*G06F 17/00* (2019.01)
*G06F 16/25* (2019.01)
*G06F 16/11* (2019.01)
*G06F 16/13* (2019.01)
*G06F 16/14* (2019.01)

(52) U.S. Cl.
CPC ......... *G06F 16/254* (2019.01); *G06F 16/116* (2019.01); *G06F 16/13* (2019.01); *G06F 16/148* (2019.01)

(58) Field of Classification Search
CPC ........ G06F 16/13; G06F 16/24; G06F 16/156; G06F 16/284; G06F 3/00
See application file for complete search history.

(56) References Cited

U.S. PATENT DOCUMENTS

| | | | |
|---|---|---|---|
| 7,111,075 B2 * | 9/2006 | Pankovcin | G06F 16/258 709/246 |
| 10,311,076 B1 * | 6/2019 | Bruhn | G06F 16/116 |
| 2002/0078216 A1 * | 6/2002 | Pankovcin | G06F 16/258 709/230 |
| 2008/0008257 A1 | 1/2008 | Yonesi et al. | |
| 2008/0082571 A1 * | 4/2008 | Sakai | G06F 16/258 |
| 2010/0299307 A1 * | 11/2010 | Kusumoto | G06F 16/116 707/609 |
| 2016/0253340 A1 * | 9/2016 | Barth | G06F 16/122 707/756 |
| 2016/0292241 A1 * | 10/2016 | Patterson | G16H 10/60 |

* cited by examiner

*Primary Examiner* — Hung D Le

(57) ABSTRACT

Managing large amounts of third party client data may require sorting through files for patterns and extracting data to create a customized user interface for the third party client. One example method of operation may include examining file names for data files stored in a database, parsing specified names and specified dates from the file names, categorizing the data files according to the specified names and specified dates, tagging the data files, and transforming content of the data files into a customized data table format associated with known client requirements.

20 Claims, 11 Drawing Sheets

FIG. 4B

AUTOMATED FILE ACQUISITION, IDENTIFICATION, EXTRACTION AND TRANSFORMATION

TECHNICAL FIELD

This application relates to data file integration and more specifically to a file organization procedure which organizes data files and identifies certain attributes prior to transforming the data into a specified data file format.

BACKGROUND

A patient at a medical facility may have undergone surgery, have a chronic condition and may require ongoing care, follow-up information, medications, visits, etc. For every patient appointment, admission, post-operation schedule, prescription, etc., there exists some data file record of such events. Data file organization is conventionally a process of identifying files by known attributes and organizing and re-organizing those files as deemed necessary. However, certain data file content that is identified in data files may require a transformation which cannot be readily performed without user assistance.

SUMMARY

One example embodiment may include a method that includes at least one of receiving a plurality of data files, loading the plurality of data files into a database, examining a portion of each of the data files, matching at least one known attribute to the portion of each of the data files, categorizing each of the data files as belonging to a specific client and a specific data type based on the matching of the at least one known attribute; and transforming content of the data files to a predefined content format associated with requirements associated with each of the specific client.

Another example embodiment may include an apparatus that includes a receiver configured to receive a plurality of data files, and a processor configured to load the plurality of data files into a database, examine a portion of each of the data files, match at least one known attribute to the portion of each of the data files, categorize each of the data files as belonging to a specific client and a specific data type based on the matching of the at least one known attribute, and transform content of the data files to a predefined content format associated with requirements associated with each of the specific client.

Still another example embodiment may include a non-transitory computer readable storage medium configured to store instructions that when executed causes a processor to perform receiving a plurality of data files, loading the plurality of data files into a database, examining a portion of each of the data files, matching at least one known attribute to the portion of each of the data files, categorizing each of the data files as belonging to a specific client and a specific data type based on the matching of the at least one known attribute, and transforming content of the data files to a predefined content format associated with requirements associated with each of the specific client.

Still yet another example embodiment may include a method that includes at least one of examining file names for a plurality of data files stored in a database, parsing specified names and specified dates from the file names, categorizing the data files according to the specified names and specified dates, tagging the data files, and transforming content of the data files into a customized data table format associated with known client requirements.

Still yet another example embodiment may include a processor configured to examine file names for a plurality of data files stored in a database, parse specified names and specified dates from the file names, categorize the data files according to the specified names and specified dates, tag the data files, and transform content of the data files into a customized data table format associated with known client requirements.

Still yet a further example embodiment may include a non-transitory computer readable storage medium configured to store instructions that when executed causes a processor to perform at least one of examining file names for a plurality of data files stored in a database, parsing specified names and specified dates from the file names, categorizing the data files according to the specified names and specified dates, tagging the data files, and transforming content of the data files into a customized data table format associated with known client requirements.

BRIEF DESCRIPTION OF THE DRAWINGS

FIG. 4B illustrates a user interface of a data transformation and management application according to an example embodiment.

DETAILED DESCRIPTION

It will be readily understood that the instant components, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments.

The instant features, structures, or characteristics of described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments, the application may be applied to many types of network data, such as, packet, frame, datagram, etc. The term "message" also includes packet, frame, datagram, and any equivalents thereof. Furthermore, while certain types of messages and signaling are depicted in exemplary embodiments they are not limited to a certain type of message, and the application is not limited to a certain type of signaling.

Example embodiments provide an automatic system configuration or software-based application which manages large amounts of data files for customized identification and transformation. For example, in the health care and medical industry, text data files from multiple external data sources, such as file transfer protocol (FTP) sources, can be identified based on defined attributes and naming conventions which are known and setup to be filtered and audited by an application as part of the file management application of example embodiments. It is important to note that file data may be any data file and type and may extend beyond health care related data which is described throughout the disclosure as one example data file type.

Continuing with the same example, the data file content can be extracted as encrypted binary data, and can also be transformed so the data elements are transformed according to defined logic. The data may be loaded as 'final data' or finalized data into specific database tables based on defined configurations which are setup and executed autonomously as the data is identified and made available.

Figure 1:
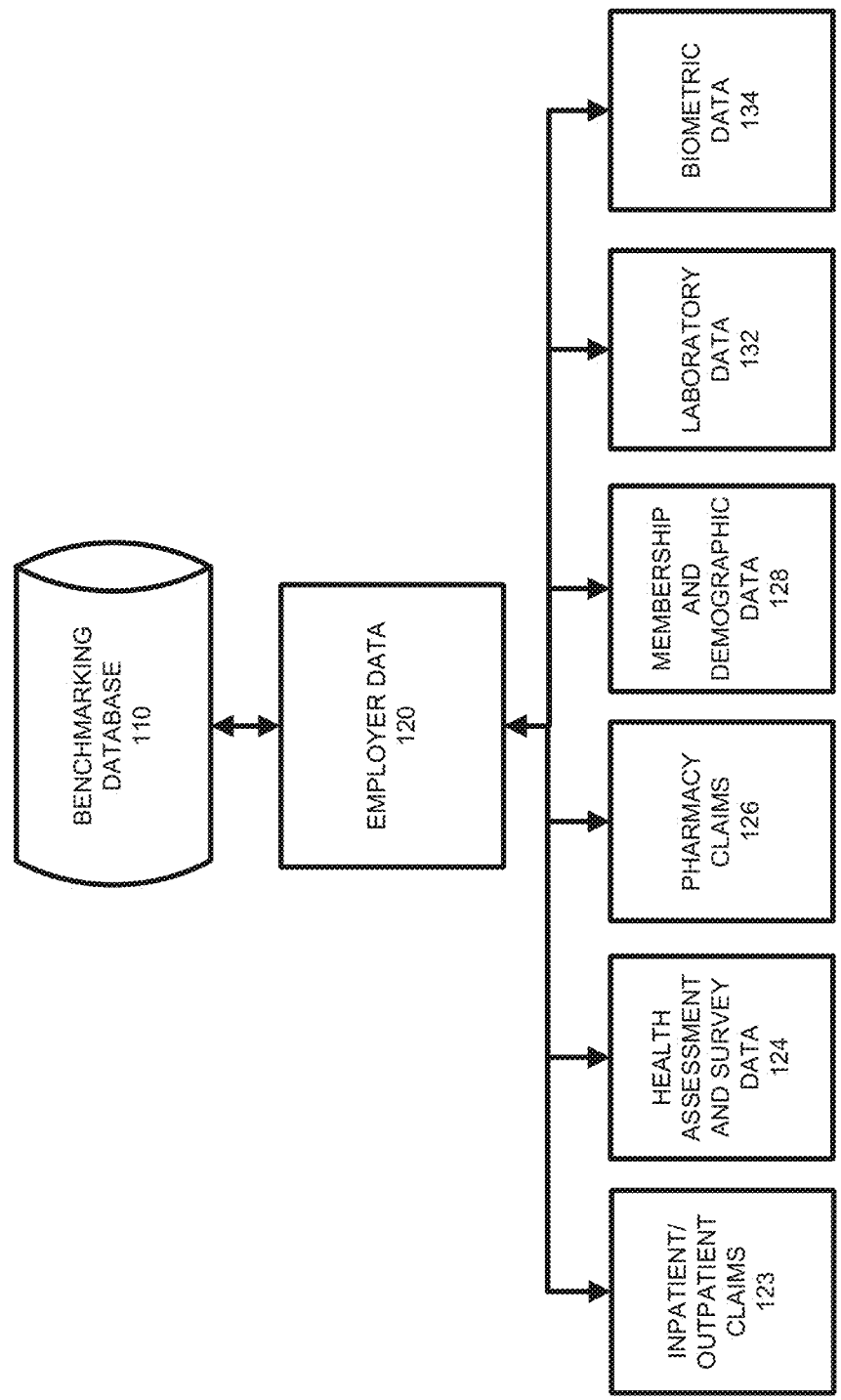
FIG. 1 illustrates a logic diagram of data analysis and data types for processed data files according to an example embodiment.

FIG. 1 illustrates a logic diagram of data analysis and data types for processed data files according to an example embodiment. Referring to FIG. 1, the network configuration 100 includes a benchmarking database 110 which stores the incoming health services research reporting data, clinical expertise data and health care management data. Such data may be used as the basis for creating core data audit procedures and establishing procedures for audit and file management. The employer data 120 may include specific data about the establishment that is utilizing the data audit procedures and file management operations. The data modules may be broken down into sectors, such as inpatient/outpatient claim 123, health assessment and survey data 124, pharmacy claim 126, membership and demographic data 128, laboratory data 132 and biometric data 134. Any of those data types may have separate data files and data file types. Some of the data may be bundled together in a common file, however, many of the data file segments may require a separate data file with a unique file name, thus requiring multiple data files and corresponding management operations.

Figure 2:
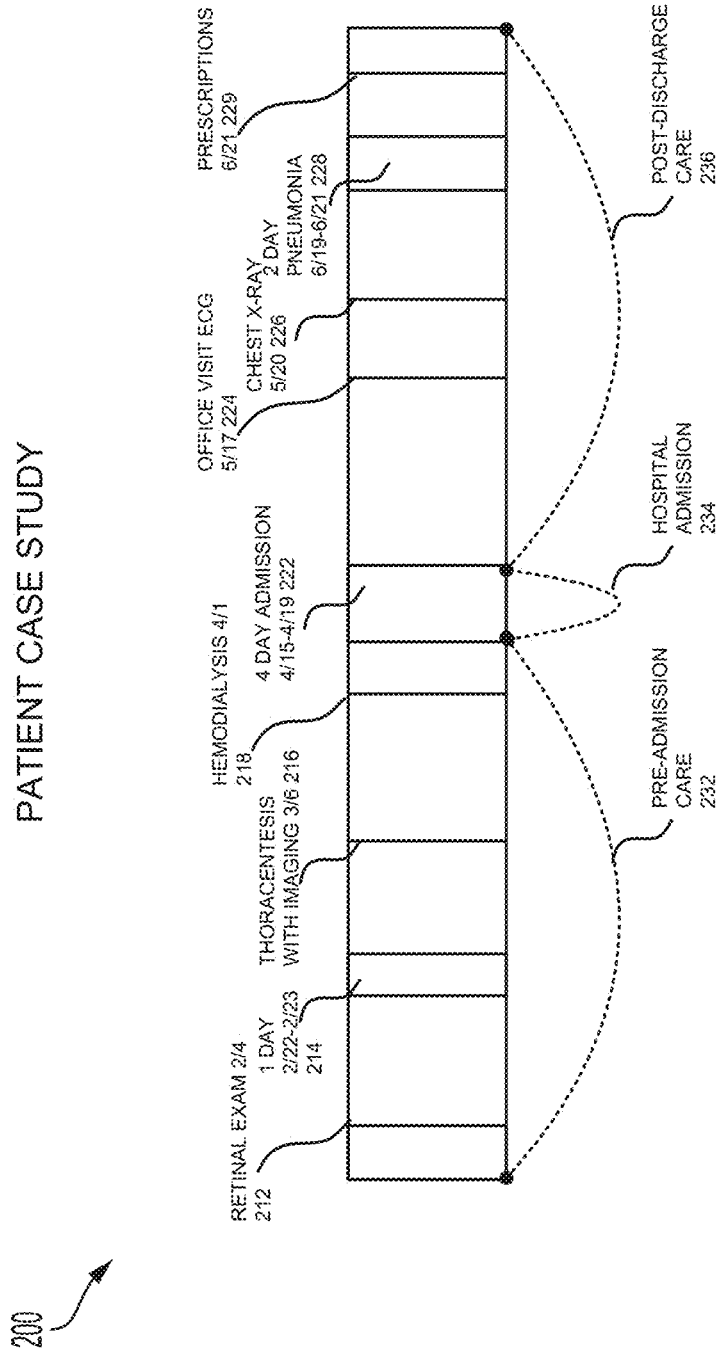
FIG. 2 illustrates a patient case study timeline according to an example embodiment.

FIG. 2 illustrates a patient case study timeline according to an example embodiment. Referring to FIG. 2, the example timeline 200 reflects a patient case study of a particular patient that is deemed to be 55 years old and experiencing certain health concerns. For example, the patient may require an admission to a medical facility (i.e., hospital). The pre-admission care 232 may have a retinal exam 212 on 2/4 and an overnight visit 214 on 2/22. Next, a thoracentesis procedure is performed with imaging 216 on 3/6 along with a hemodialysis 218 on 4/1. The hospital admission is then identified 234 as a four day visit 222 from 4/15 to 4/19. Lastly, the post-discharge care 236 is identified as including a visit 224, an x-ray 226, a pneumonia condition 228 and a set of prescriptions 229. Each of these instances on the patient timeline are included in one or more data files which must be identified, tracked and processed to ensure a central treatment application can extract the available data to plan a course of treatment for the patient.

Figure 3:
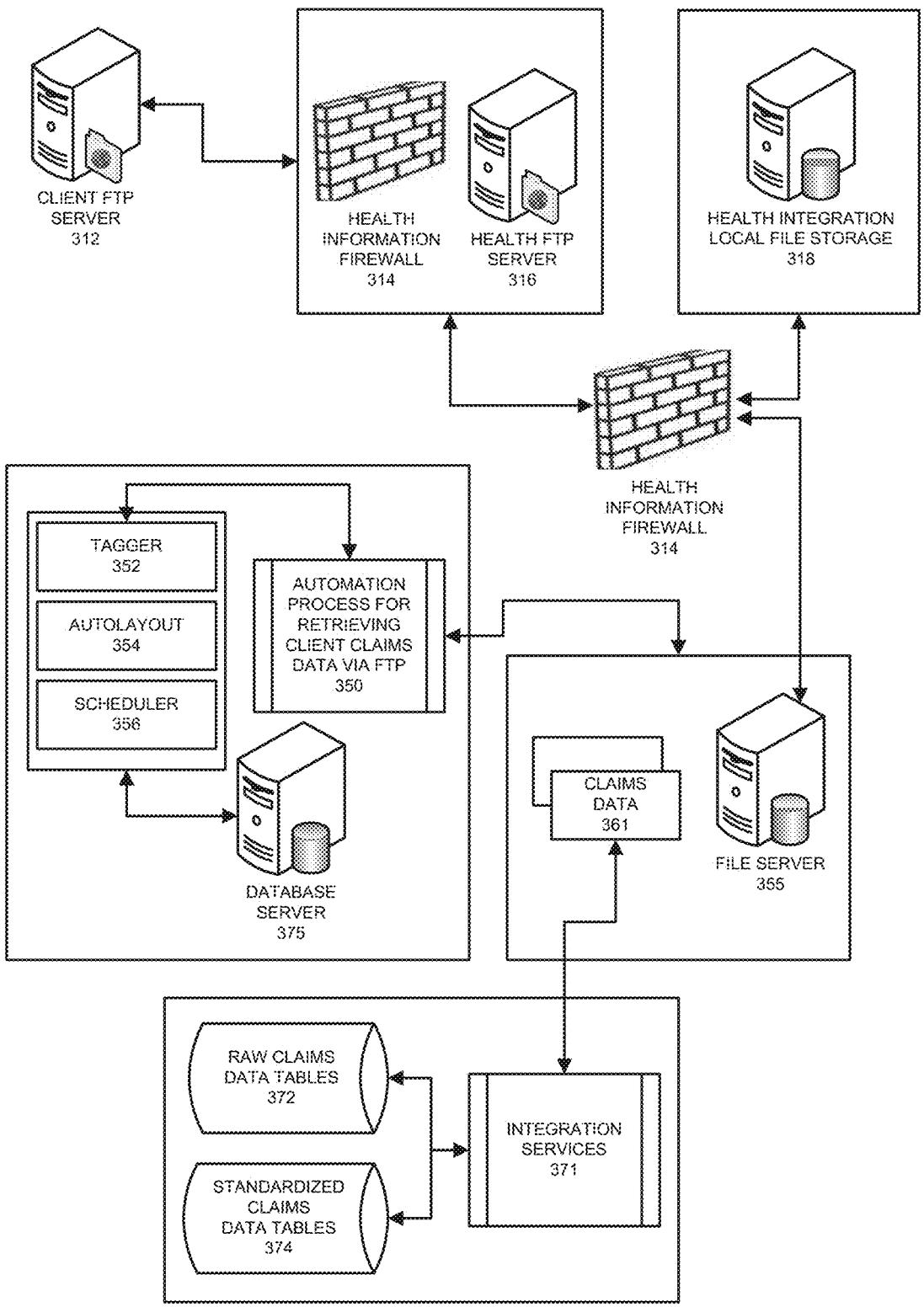
FIG. 3 illustrates a network diagram of a health care computer and data management configuration according to an example embodiment.

FIG. 3 illustrates a network diagram of a health care computer and data management configuration according to an example embodiment. Referring to FIG. 3, the network 300 includes a procedure for automation of data loading. In operation, the clients 312, such as sources of customer data files may send medical claims and other files to a secure ftp health server 316 guarded by a firewall 314. The data file processing facility 318 may provide local file storage and various services which offer data management services and data outsourcing. The on-site facility may include a file server 355 which receives the claim data 361 and manages the integration services 371 of the database including raw claims in a first data table format 372 and ultimately via a standardized claims data table 374. The processing center may include a database server 375 which applies the automation process 350 for retrieving and transforming the client claims and other data via a FTP procedure. The components of the application 350 may include a "tagger" 352, an "auto layout" module 354 and a scheduler 356 each of which is part of the file processing procedure.

According to example embodiments, a data file acquisition procedure may include identifying data files, which are received via any of two main ways, such as receiving some data text files via a standard FTP by a "push" command where a client application uploads data to a local FTP server. Another option for receiving data files may be a 'GetEx' type command where others are received by "pull", where the system scans client FTP sites for new, unprocessed files. GetEx jobs are created using a custom user interface. The system application may support the following FTP protocols: 'FTP', 'SFTP', 'FTPS Implicit', 'FTPS Explicit', etc. Also, "password" and "public key" SSH authentication types may be supported. In operation, connections can be made to any FTP port. A GetEx command scans external FTP sites multiple times per day, such as three times per day, however any frequency for scanning can be used, and any new files are automatically downloaded and saved to a secure location as a cluster of files requiring pre-processing or pre-organization management procedures. All activity and errors are logged, for example, as files are identified by size and file name and other file attributes, the logs will be updated to reflect the new data file attributes. At this stage, a new pre-analysis can be performed to log the file name attributes which are being audited and filtered. For example, any file name that includes matching information that matches the audit criteria data may be temporarily logged as successful vs. unsuccessful for data files with no recognizable file naming convention. Those files with unidentifiable data file names may be logged as errors.

With regard to the data file tagging, files received via standard FTP and "GetEx" are placed into secure folders, the "tagger" jobs are created using a custom user interface. Each job processes files in a particular folder. Files can be encrypted (PGP), compressed (".zip" or ".gzip"), EXCEL (all versions), as well as plain text files and other file types. File identification is performed using regular expression patterns ("Regex"). One job "sequence" entry is created for each step of the identification process. Examples of file naming "patterns" include "decrypt": (?i)NEWCSC_HEALTHADVOCATE_Membership_(\d{6})_(\d{4})_(\d{2})[.]zip[.]pgp"; "unzip": "(?i)NEWCSC_HEALTHADVOCATE_(\d{4})_(\d{2}).zip"; "tag": "(?i)NEW CUSTOMER SERVICE COMPANIES_ASRL_Medical_(\d{6})_(\d{4})_ (\d{2})[.]txt"; and "tag": "(?i)NEW CUSTOMER SERVICE COMPANIES_ASRL_Membership_(\d{6})_(\d{4})_(\d{2})[.]txt". Files are tagged with properties such as but not limited to client, type, carrier, data year and data month. The "tagger" permits flexibility in processing data files as efficiently and accurately as possible. Files can be checked for truncation by examining the EOF characters (end-of-file). This check can be skipped for files containing non-standard EOF characters. Files can be modified to enable subsequent automatic loading. For example, "Ragged-right" delimited files can be padded with additional delimiters. Header rows can be removed if these rows do not contain data and cause loading errors. Files which are sent with the same filename can have timestamps appended to the filename to ensure uniqueness during subsequent auditing procedures. Once the files are identified, decrypted and decompressed the files are loaded into an encrypted database as binary large objects (BLOBs). It is from this database that the data in the files is subsequently parsed and loaded into the database tables. All activity and errors are logged.

Next, an "auto layout" procedure is a dynamic, data-driven application written on top of a single SQL server SSIS (SQL server integration services) package, which scans the encrypted database for any new files, and then extracts, transforms and loads the data into database tables customized for end client specifications. When data file processing jobs are run for the first time, the database tables are created automatically. Subsequent operations populate the tables. Normally, SSIS packages must have all file connections, data connections, file attributes (i.e., delimiter, text qualifier, lines to skip, column names, data types, etc.) pre-defined. In this case, one SSIS package would normally be needed for each file layout resulting in several hundreds of packages. With "auto layout", however, every aspect of the job, such as a source file location, SQL server destination connection, file type, column delimiters, text qualifiers, column names and data types, and transformations to the data can be configured using a custom user-interface. Certain "auto layout" jobs can have multiple destinations in cases where data for multiple clients are contained within the same file, or data for multiple "types" (i.e., medical, pharmacy, etc.) are contained within the same file. This means that data from a single text file can be split into multiple database tables using a simple "where" clause entered in the user interface.

A column definition can be imported from a layout document. A list of column names can be added along with a corresponding list of column widths and a list of data types. With a one button click, hundreds of column definitions are created. Column values can be "transformed" using recursively-applied "modifiers". For example, a text file may contain a date value with leading spaces. Two "modifiers" can be used, which first removes the spaces, and then converts the date variable using a CAST statement. The number of modifiers is limited to the SQL server maximum recursion depth, which is usually '32'. The application has to process records in many different formats from different companies due to a lack of standardization.

The data in these records must ultimately be normalized and placed in a database for use analysis, etc. The most laborious of which is to write separate software for each record source and each format from that source. Each source specific software package needs to handle the data format from that source and normalize the data into a common database format. Alternatively, a software package can be used that permits the user to configure how the records in various formats will be mapped into the system database. This requires the data sources, file formats, etc. be matched and involves pattern matching. The archive files must be recognized that are being delivered to the system via FTP, etc. Then, the file or files have to be extracted in those archives for processing. Also, the data in the files has to be normalized and imported into the system database. The capabilities of this system enable the processing of new file formats from new or existing data sources without the writing of additional software.

Figure 4A:
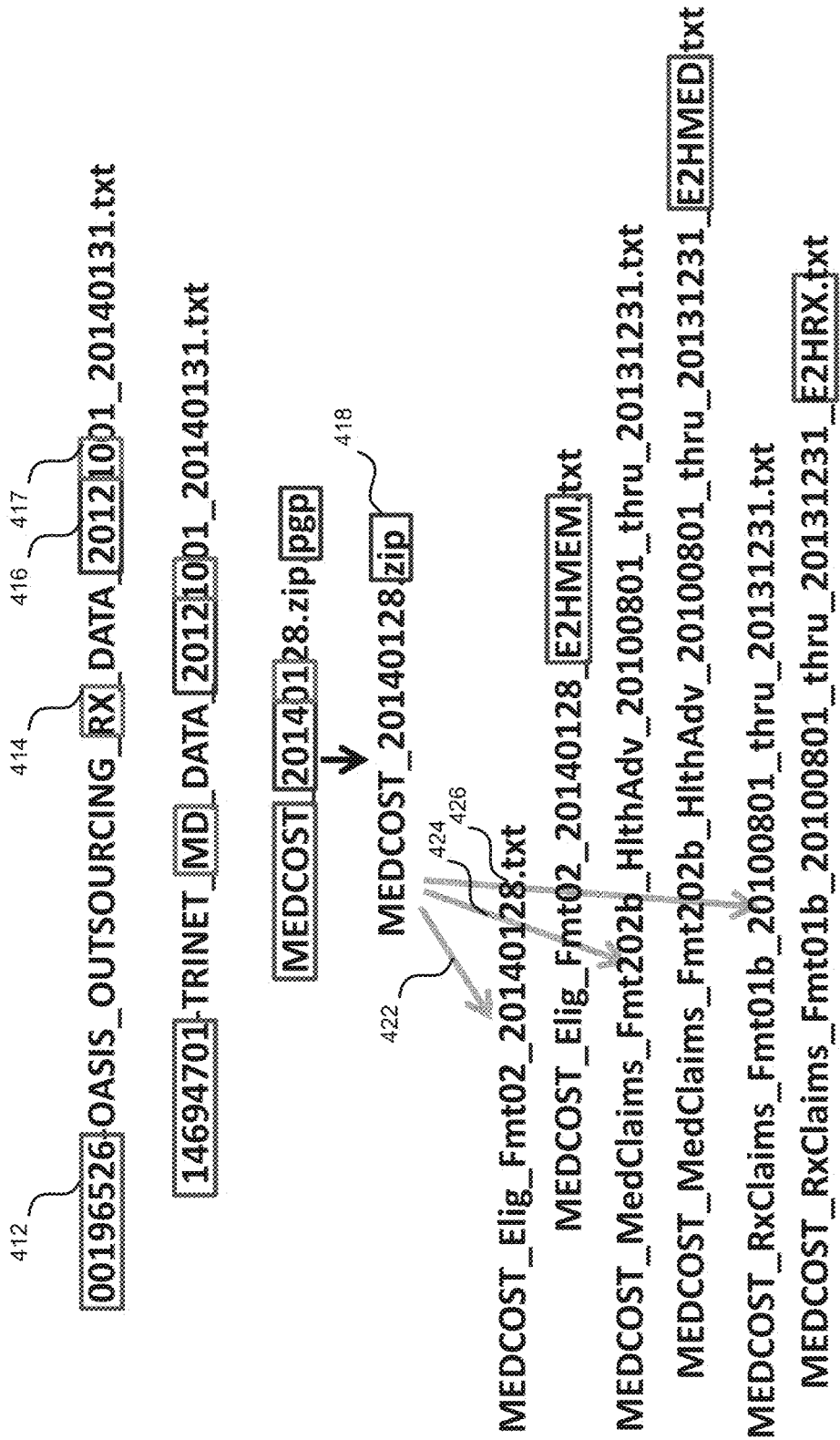
FIG. 4A illustrates a tagging and data file matching and extraction procedure according to an example embodiment.
Figure 4B:
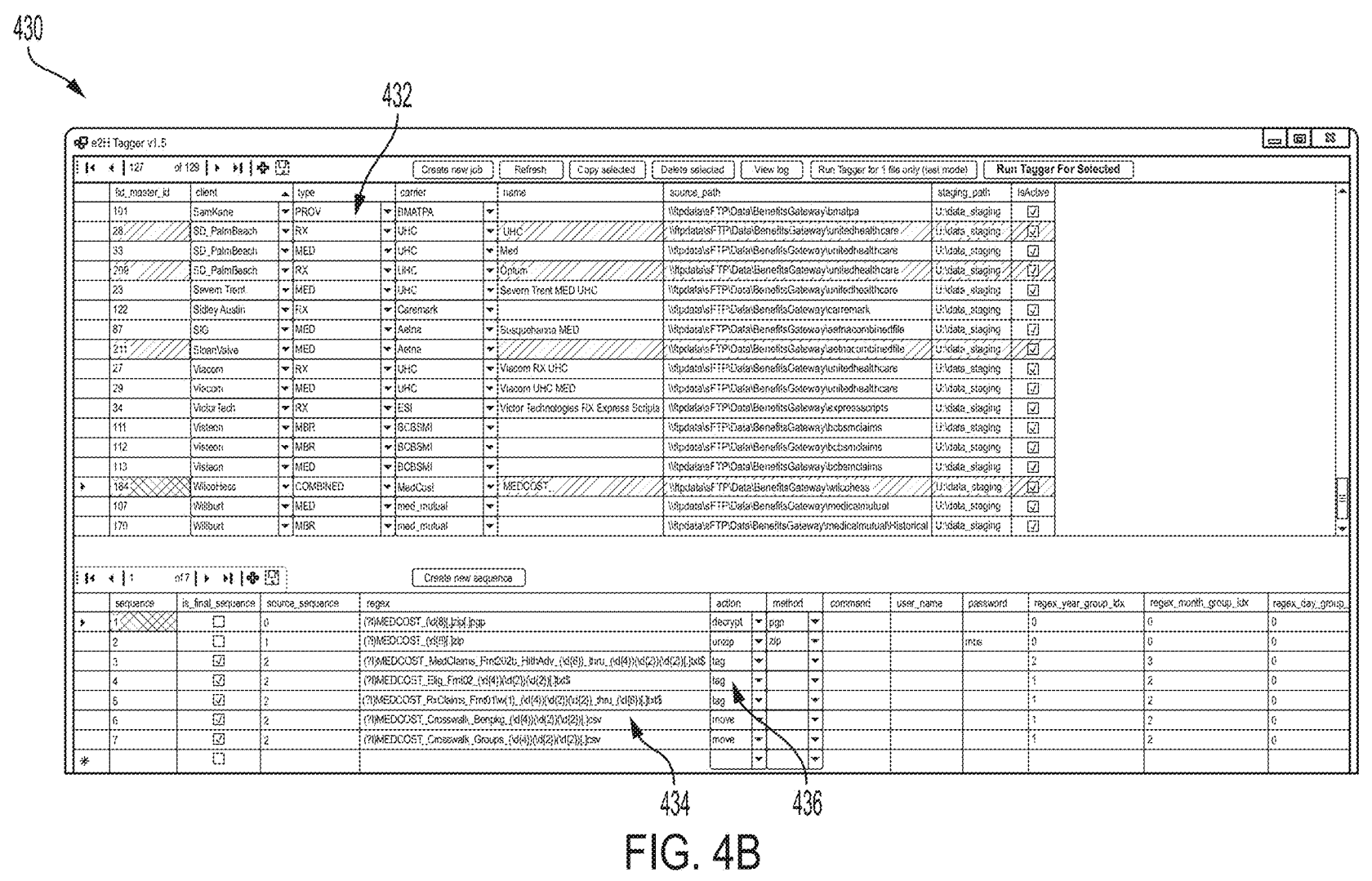

FIG. 4A illustrates a tagging and data file matching and extraction procedure according to an example embodiment. Referring to FIG. 4A, the audited parameters included in the file names include serial numbers 412 which may map to categories, acronyms, such as RX and MD 414 which may map to specific procedures and claim types, dates 416 and 417, and file types 418, which may map to extraction procedures which extract additional files 422, 424 and 426. The data file mapping and extraction may include organizing the files for transformation so the data in the files can be placed in the appropriate tables and columns. For example, in FIG. 4B a user interface for "tagger" jobs 430 is illustrated to include a data transformation and management application according to an example embodiment. The job definition 432 is predefined for data files discovered in a particular location in a secure file system. The file name patterns for each step are included 434 in the file sequence configuration along with a particular action, such as tag, decrypt, unzip and/or move.

Figure 4C:
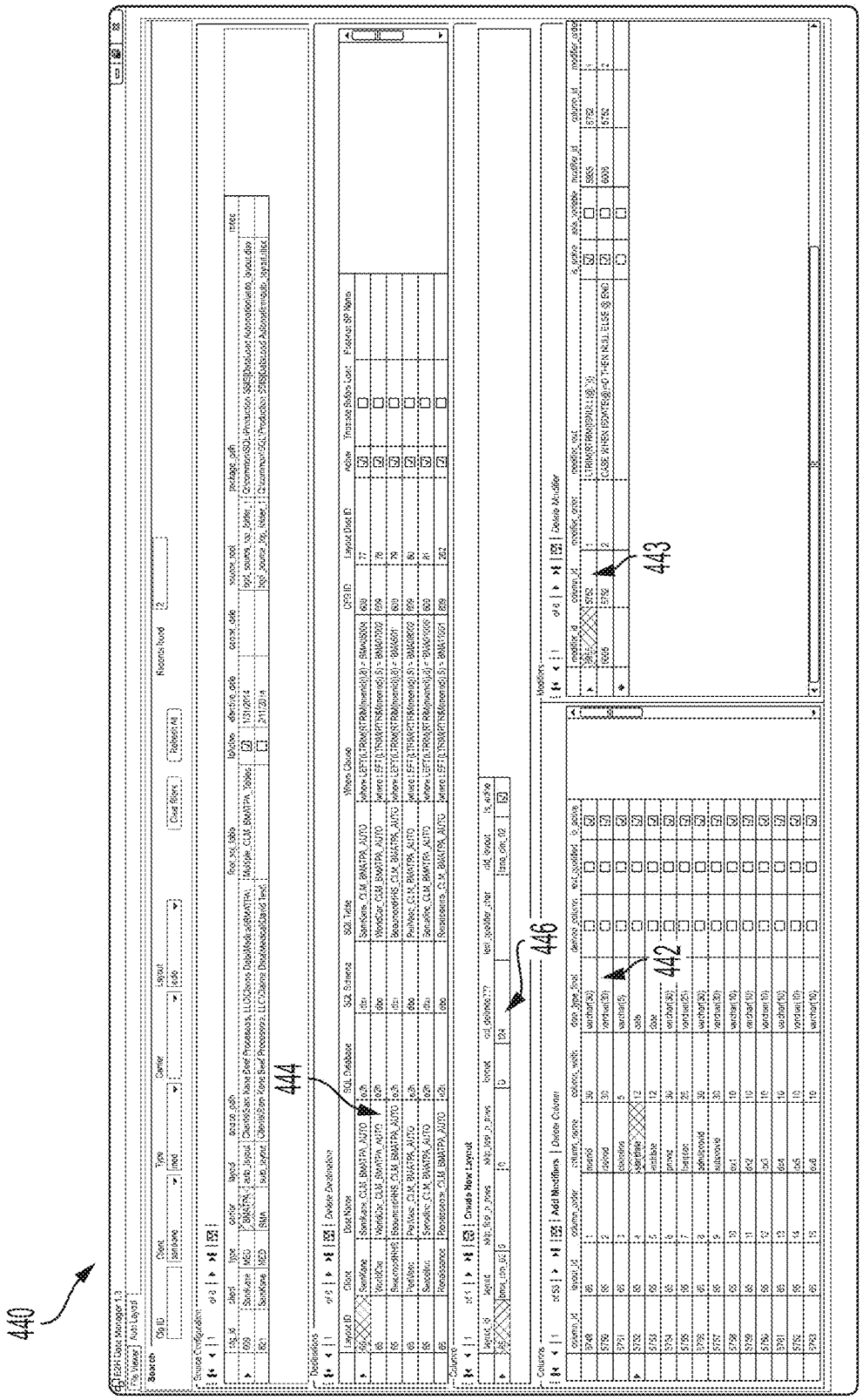
FIG. 4C illustrates a user interface of a data file transformation and integration procedure according to an example embodiment.

FIG. 4C illustrates an "auto layout" user interface of a data file transformation and integration procedure according to an example embodiment. Referring to FIG. 4C, the interface 440 includes various database tables 444 which will be populated with parsed text file data based on structural file attributes 446, column mappings 442 and "modifiers" 443. A column definition may be stored as metadata 442.

Figure 4D:
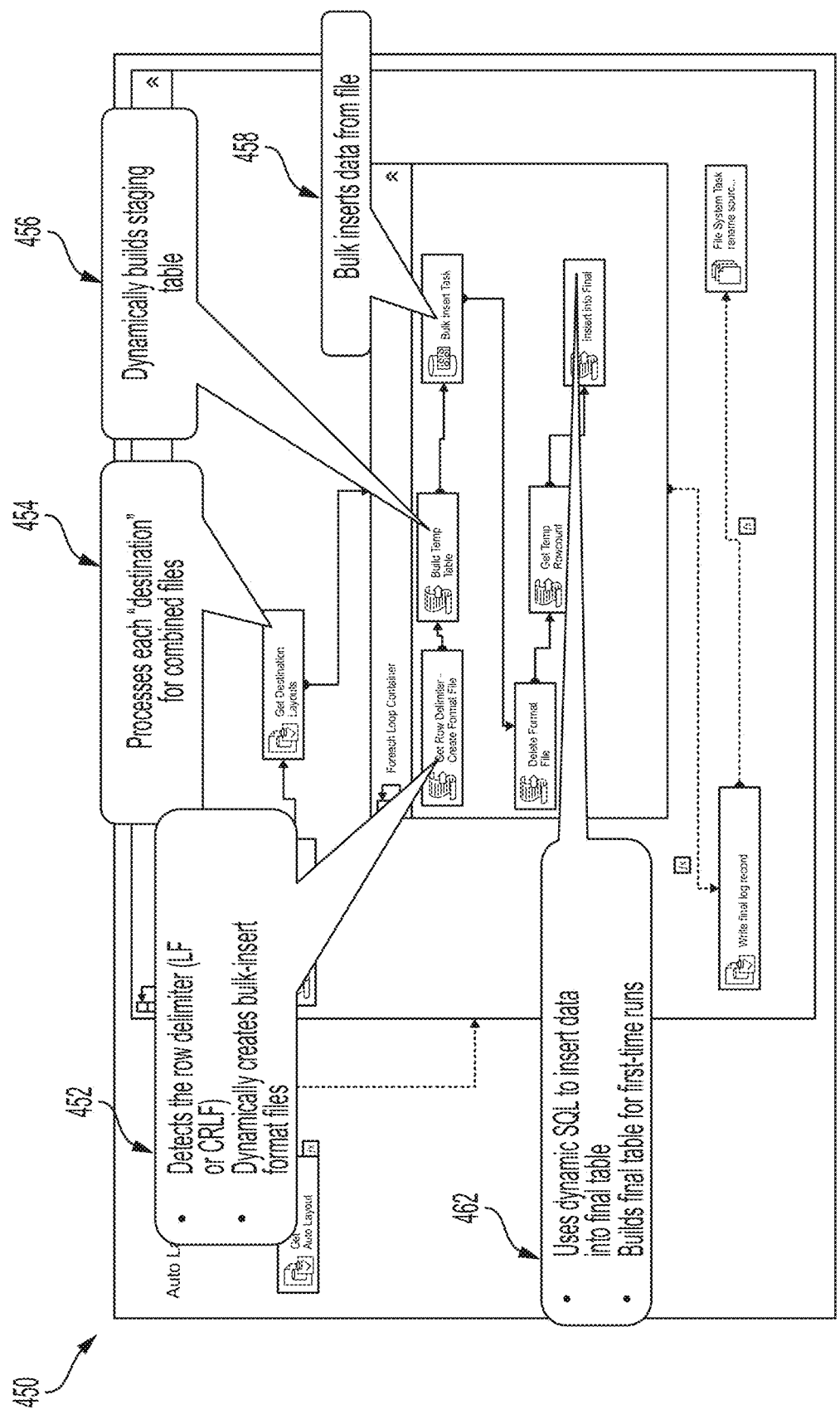
FIG. 4D illustrates another user interface of a data file transformation and integration procedure according to an example embodiment.

FIG. 4D illustrates a data-driven data file transformation and integration procedure according to an example embodiment. Referring to FIG. 4D, the user interface 450 includes a set of scripts which execute using settings entered into the user-interface 440. The functions may include processing each destination for combined files 454, detecting a row delimiter, such as LF or CRLF or other delimiters, and creating a bulk-insert format file(s) 452, building a temp table 456 and performing a bulk insert of the data from the file 458. Other operations may include using a dynamic operation to insert data into a final data format 462 and building a new table if a first run is being performed.

Figure 5:
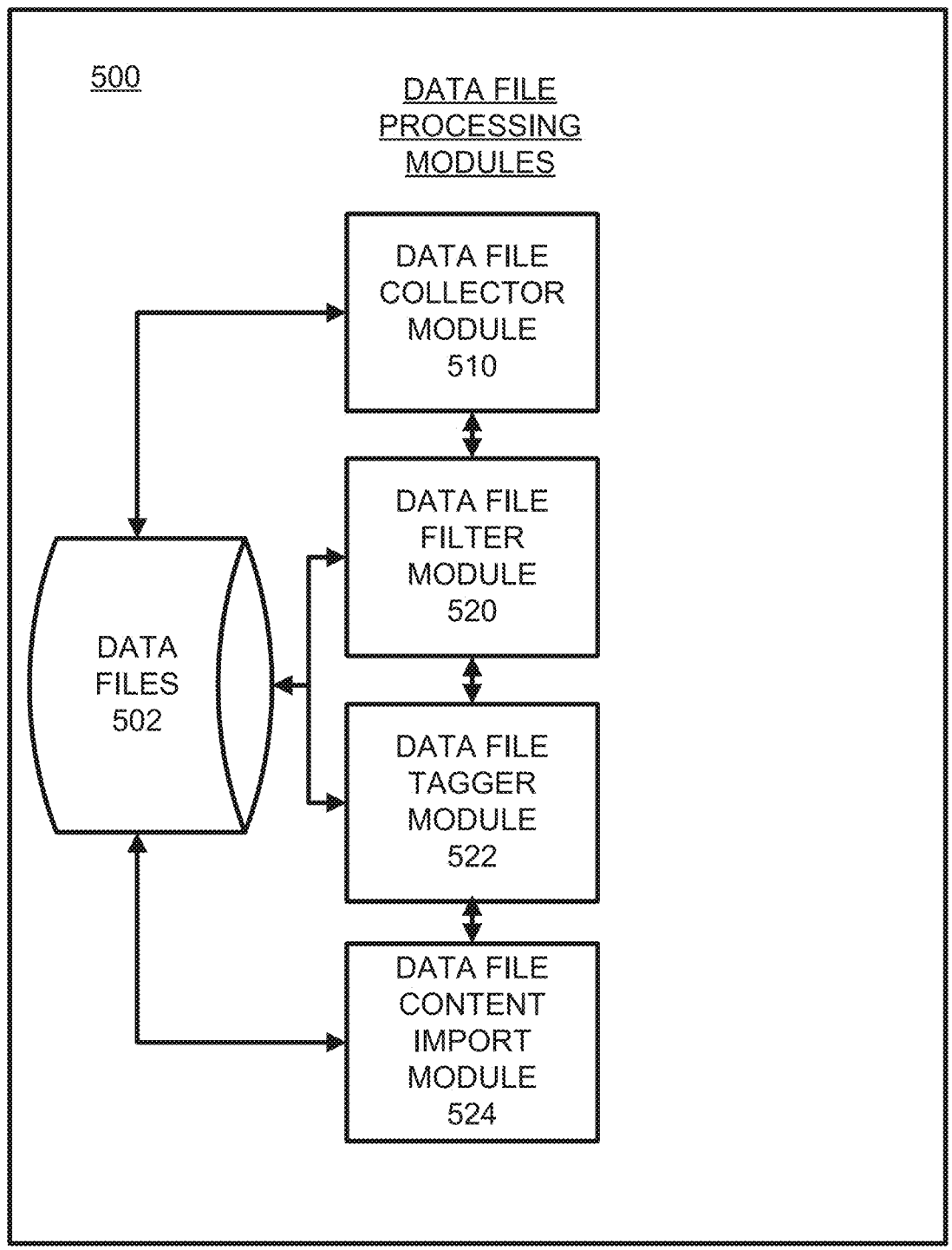
FIG. 5 illustrates a data file management configuration according to an example embodiment.

FIG. 5 illustrates a data file processing system 500 which includes various modules which process the raw data files 502. The data file collector 510 is responsible for receiving data files and logging the files to be processed and transformed. The data file filter module 520 performs the various audits against the file names to identify the categories and content of the data files. The "tagger" module 522 will then designate the data file attributes as belonging to a particular category or other identifier in a new table and the import module 524 will populate the data into the new table or existing table depending on the recent import transactions.

In operation, the data file management system of FIG. 5A may acquire a data file(s), identify data file type(s) and pre-process the data files before storing them in a secure database. Next, a data file type may be identified and processed according to configured rules for the file type. Each file type may have different rules, for example, a zip file may first undergo an unzip and/or extraction procedure. Also, certain file types may be modified to create a new file type format or to have data modified prior to transformation and extraction. All data is generally decrypted, since all medical files are typically encrypted. Next, data file(s) are pre-processed as BLOBs according to rules for the file type extraction. The data files are pre-processed in an encrypted database, such as a SQL database, however, other data file encryption methods may also be used. Data files are extracted from the encrypted database and transformed and loaded as data elements (rows and columns) into a normalized database.

Once the files are stored, the encrypted database can be scanned for new files by examining a status field. The data can be transformed for import into the normalized database according to rules for the corresponding "auto layout" job. The transformed data can be inserted into one or more tables in the normalized database.

According to one example, the text data files are a primary data source for medical claims and member data received from health insurance carriers. The data is provided to produce dashboards and reports for the clients. The data is also used to build a "standard" database to compare client data to the total population. The data is also used with a web application, which provides members with out-of-pocket cost estimates for various medical procedures based on demographics, such as a zip code and current benefit status. The FTP sources include the FTP servers owned by client carriers. Attributes used to identify the client data may include attributes of the file itself not the data contained in the file. One example is the file attribute "modified date".

Thousands of files placed in a single folder each month must be identified by matching the name of the file to a defined pattern, which corresponds to a particular client and "type" either medical claims, pharmacy claims, vision claims, etc., or member data. For example, for a file named "NEWCSC_HEALTHADVOCATE_201308.ZIP.PGP", the "tagger" module searches through the outstanding jobs, and finds a REGEX (regular expression) pattern of "(?i)NEWCSC_HEALTHADVOCATE_(\d{4})_(\d{2}).zip.pgp". This pattern indicates the following: "(?i)" means to perform a case-insensitive search, "NEWCSC_HEALTHADVOCATE" is a literal text match, "(\d{4})" indicates to match any 4 numbers, "(\d{2})" indicates to match any 2 numbers, and ".zip.pgp" literal text match. The "tagger" now knows that this file is for a specific company and purpose and for a particular medical carrier, and it is a combined file, meaning it contains multiple "types" of files, in this case medical claims and membership data.

Now that the "tagger" job has been identified, the file can be processed by cycling through all of the job "sequences" and performing actions on the file. Since the file in this example is a ".pgp" file (encrypted), the action of the first "sequence" is to decrypt the file, and then save the resulting decrypted file to a staging file location for further processing. The filename of the decrypted file is "NEWCSC_HEALTHADVOCATE_201308.ZIP". One of the "patterns" for "sequence 2" of this job is "(?i)NEWCSC_HEALTHADVOCATE_(\d{4})_(\d{2}).zip", which matches the decrypted file. As a result, the "tagger" processes this file as a compressed file, by executing the action prescribed for this pattern which is "unzip" using the "zip" protocol. The resultant files are placed in a staging file location for subsequent processing by "sequence 3". In this case, there are three resultant files: 1. NEW CUSTOMER SERVICE COMPANIES_ASRL_Medical_201308.txt (medical claims), 2. NEW CUSTOMER SERVICE COMPANIES_ASRL_Membership_201308.txt (membership), and 3. NEW CUSTOMER SERVICE COMPANIES-ASRL Balancing Report.RTF (checksum report). The "tagger" then moves to "sequence 3" and starts to check patterns against these filenames. The "tagger" finds a pattern, "(?i)NEW CUSTOMER SERVICE COMPANIES_ASRL_Medical_(\d{4})_(\d{2})[.]txt", which identifies the first file as a medical claims file, and directs the application to "tag" the file. This "tag" would then be used by 'AutoLayout' to identify that this file needed to be loaded. HOWEVER, since the files are stored store the file as a "BLOB" (binary large object) in the encrypted database. When it's first loaded, a data flag is set to "0", which notifies "auto layout" that the file has not yet been loaded.

In the pattern: "(?i)NEW CUSTOMER SERVICE COMPANIES_ASRL_Medical_(\d{4})_(\d{2})[.]txt", since we need to know the month and year of the data in these files, the "tagger" uses the regex "groupings" to identify the month and year. "groupings" are the portions of the regex pattern set off by opening and closing parentheses. The final "grouping" in this case is "(\d{2})". The "tagger" pattern configuration identifies the value in this grouping as the number of the data MONTH. The second-last grouping, "(\d{4})", is identified as the data YEAR. In some cases, the filename does not contain the data month and year. In these cases, the physical file's modified date is used as the data year and month. Regardless of how the month and year data is obtained, a setting in the "tagger" can subtract months from the identified month and year, in cases where the data in the file is one or more months older than the identified month and year. For example, for a file with a month and year of 2016-05, but the data is actually from April, 2016, the "month adjust" would be set to a value of "1", which instructs "tagger" to set the month and year to "201604", reflecting the actual month. The "tagger" then uses this year and month to build a virtual file path, such as: \\engagesql\vault\Clients\National Electronics Warranty (NEW)\Claims Data\Medical\Anthem\2013-08\NEW CUSTOMER SERVICE COMPANIES_ASRL_Medical_201308_loaded.txt. This is not a physical path, since the files are not loaded onto a file system, but it is a virtual path which permits the database interface to present the user with a hierarchical navigation structure for managing the files.

In general, the file naming convention and modified naming convention are examined in this file organization procedure. Once the "tagger" loads the file as a BLOB into the encrypted database, the "auto layout" function then imports the file data into "normal" database tables, transforming the raw text into data elements structured as columns and rows.

Figure 6A:
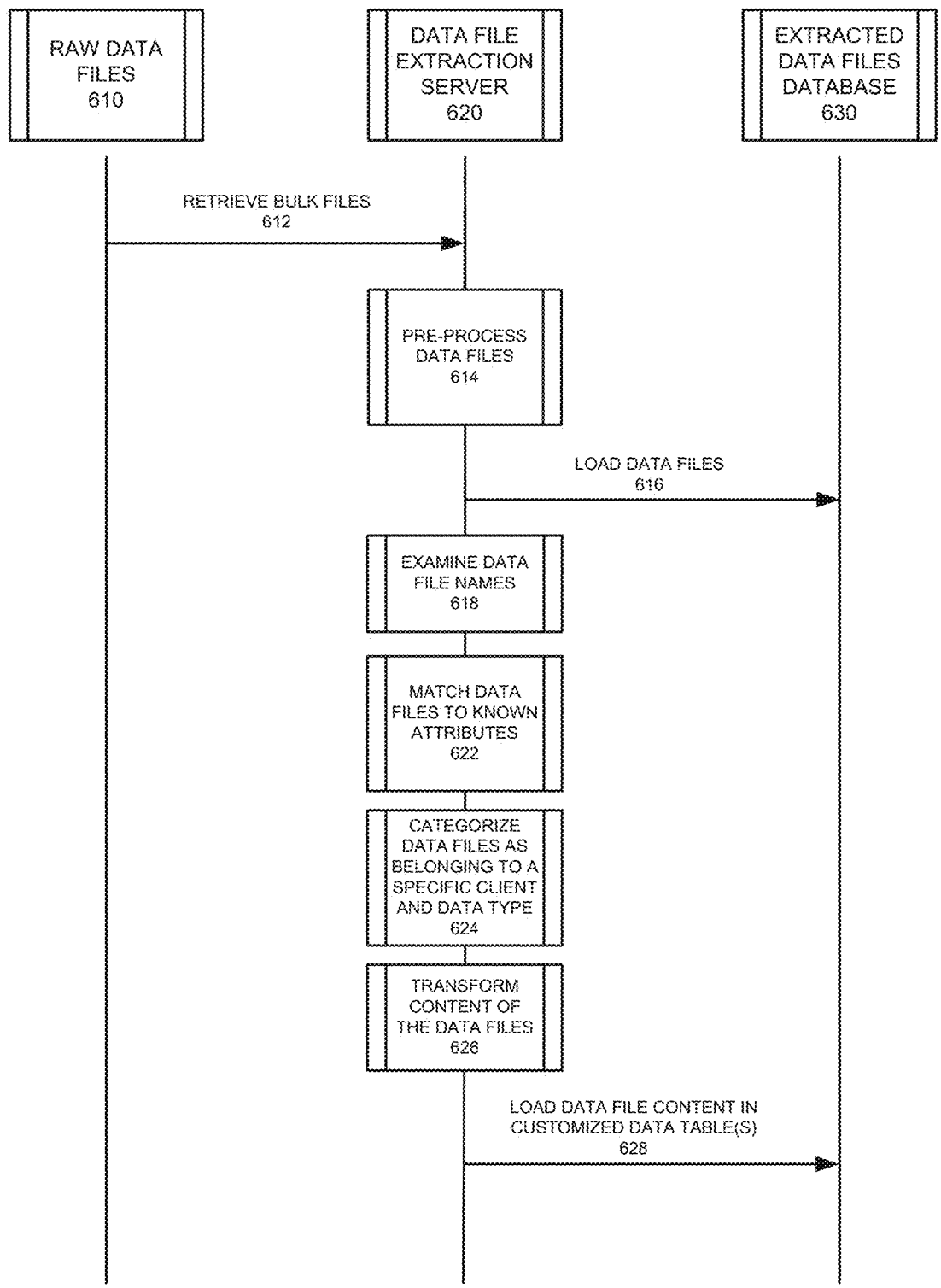
FIG. 6A illustrates a system signaling diagram of a data file management procedure according to example embodiments.

FIG. 6A illustrates a system signaling diagram of a data file management procedure according to example embodiments. Referring to FIG. 6A, the system includes raw data files 610 which may be sent to the data file processing server 620 for processing and which may be sent to a database 630. In operation, the bulk files may be received 612 and loaded into a database 616. A pre-processing function 614 may be performed to analyze the data files and examine a portion of each of the data files, such as metadata or the file names or other data file parameters. The file names are examined 618 and a matching procedure 622 may be performed to match at least one known attribute to a portion of each of the data files. The files can be categorized as belonging to a specific client and a specific data type 624 based on the matching of the at least one known attribute, and content of the data files can be transformed 626 to a predefined content format associated with requirements associated with each of the specific clients. The data can be loaded into the customized data tables 628 for client requirements.

Also, identifying a data file type may provide identifying at least one compressed file type, and decompressing the data files with the compressed file type, and extracting a plurality of decompressed data files and identifying a data file type associated with each of the plurality of decompressed data files. Examining a portion of each of the data files may provide processing a file name of each of the data files. The specific data type may provide at least one of a claim type and a member data. Matching the at least one attribute to the portion of each of the data files may provide matching a predefined group of numbers in the data file names to a known set of numbers or a predefined set of text in the data file names to a known set of text. In addition, a flag is set to zero for each of the data files when the data files are loaded in the database.

Figure 6B:
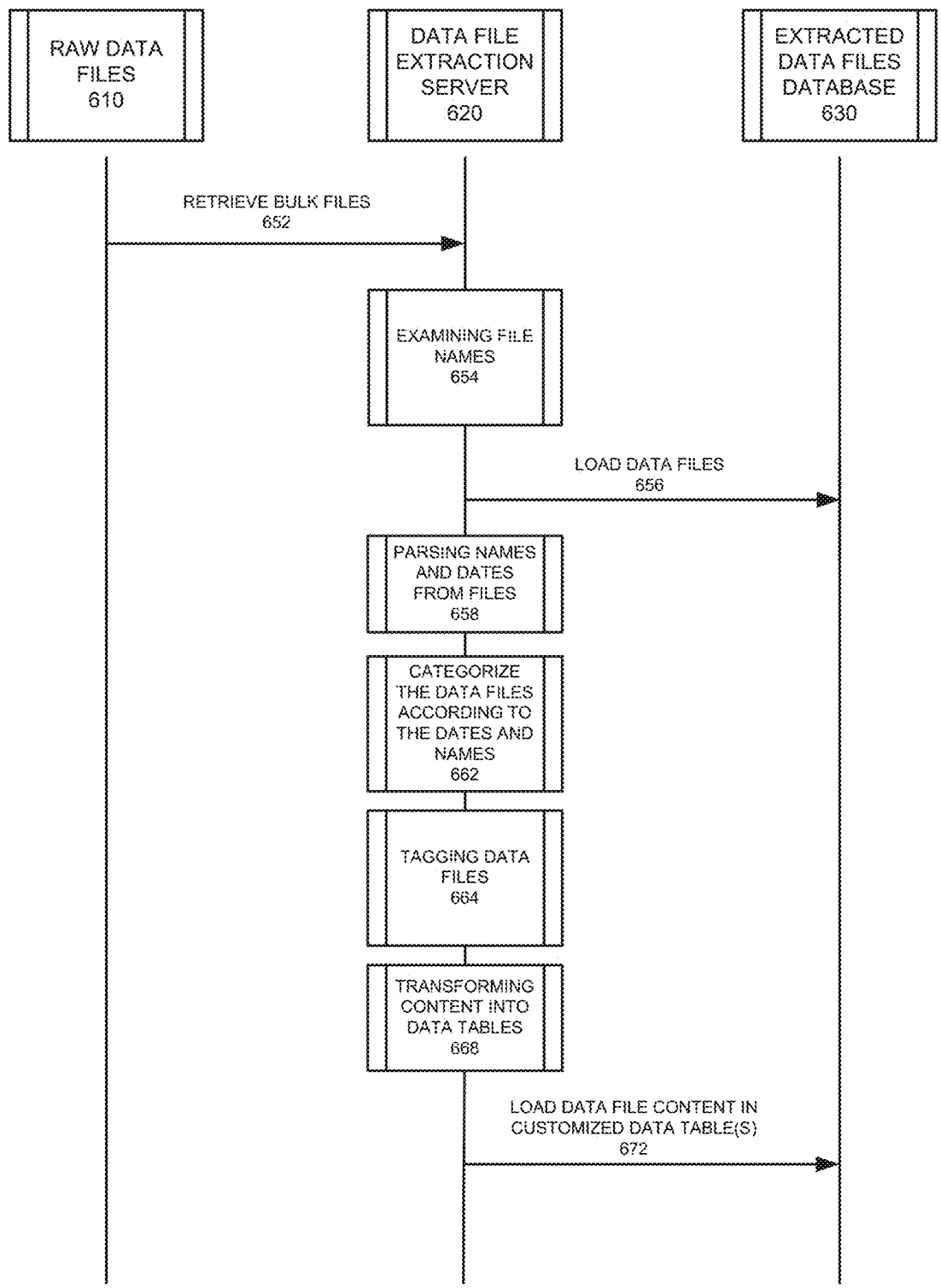
FIG. 6B illustrates a system signaling diagram of a data file content extraction procedure according to example embodiments.

FIG. 6B illustrates a system signaling diagram of a data file content extraction procedure according to example embodiments. Referring to FIG. 6B, the example 650 includes the bulk files being received 652 and examining file names for a plurality of data files 654. The data files are loaded 656 into the database and the names of the files are parsed 658, the data files are categorized according to the specified names and specified dates 662, and the files are tagged 664 and the content is transformed into a customized data table format 668 and loaded into the customized table format 672 associated with known client requirements.

Transforming content of the data files into the customized data table format associated with the known client requirements may include performing a bulk insert from the plurality of data files into the customized data table format. The data files are tagged and loaded into the database as a binary large object (BLOB) and a year and month (or day, quarter, etc.) from the data file names is also identified. The tagging of the data files may include labeling the data files with one or more of a client identifier, a type identifier, year identifier and a month identifier. Also, a column or row may be loaded in a table with content of the tagged data files based on the data file labels. The names of the data files can be matched to known patterns with a client category and a type category.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 7 illustrates an example network element 700, which may represent any of the above-described network components, etc.

Figure 7:
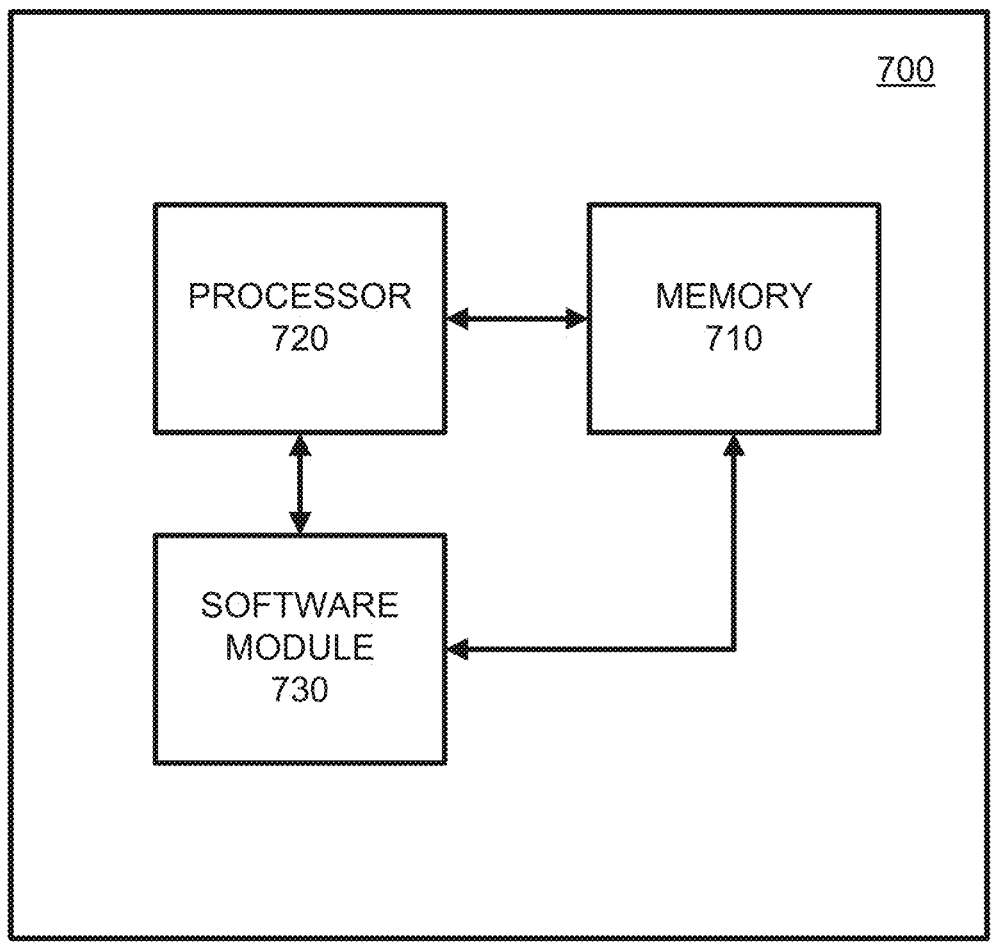
FIG. 7 illustrates a system network entity configured to store instructions and data necessary to perform and enact any of the enclosed embodiments.

As illustrated in FIG. 7, a memory 710 and a processor 720 may be discrete components of a network entity 700 that are used to execute an application or set of operations as described herein. The application may be coded in software in a computer language understood by the processor 720, and stored in a computer readable medium, such as, a memory 710. The computer readable medium may be a non-transitory computer readable medium that includes tangible hardware components in addition to software stored in memory. Furthermore, a software module 730 may be another discrete entity that is part of the network entity 700, and which contains software instructions that may be executed by the processor 720. In addition to the above noted components of the network entity 700, the network entity 700 may also have a transmitter and receiver pair configured to receive and transmit communication signals (not shown).

Although an exemplary embodiment of the system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:
   parsing specified names and specified dates from file names of a plurality of data files stored in a database;
   identifying a defined pattern associated with a particular client and a particular type of data;
   identifying a data pattern of each data file of the plurality of data files;
   identifying data files, of the plurality of data files, associated with the particular client based on the parsed specified names and the parsed specified dates conforming to the defined pattern associated with the particular client and the particular type of data;
   tagging the data files; and
   transforming content of the data files into a customized data table format associated with requirements of the particular client.

2. The method of claim 1, wherein transforming content of the data files into the customized data table format associated with the known client requirements comprises performing a bulk insert from the plurality of data files into the customized data table format.

3. The method of claim 2, further comprising loading the data files into the database as a binary large object (BLOB).

4. The method of claim 1, further comprising:
   identifying a year and month from the data file names; and
   logging a status of each of the data files.

5. The method of claim 3, wherein tagging the data files comprises labeling the data files with one or more of a client identifier, a type identifier, year identifier and a month identifier.

6. The method of claim 5, further comprising loading a column or row in a table with content of the tagged data files based on the data file labels.

7. The method of claim 6, further comprising matching names of the data files to known patterns comprising a client category and a type category.

8. An apparatus comprising:
   a processor configured to:
     parse specified names and specified dates from file names of a plurality of data files stored in a database;
     identify a defined pattern associated with a particular client and a particular type of data;
     identify a data pattern of each data file of the plurality of data files;
     identify data files, of the plurality of data files, associated with the particular client based on the parsed specified names and the parsed specified dates conforming to the defined pattern associated with the particular client and the particular type of data;
     tag the data files; and
     transform content of the data files into a customized data table format associated with requirements of the particular client.

9. The apparatus of claim 8, wherein the processor transforms content of the data files into the customized data table format associated with the known client requirements comprises a bulk insert from the plurality of data files into the customized data table format.

10. The apparatus of claim 9, wherein the processor is further configured to load the data files into the database as a binary large object (BLOB).

11. The apparatus of claim 8, wherein the processor is further configured to:
    identify a year and month from the data file names, and
    log a status of each of the data files.

12. The apparatus of claim 11, wherein the processor tags the data files via labels applied to the data files with one or more of a client identifier, a type identifier, year identifier and a month identifier.

13. The apparatus of claim 12, wherein the processor loads a column or row in a table with content of the tagged data files based on the data file labels.

14. The apparatus of claim 13, wherein the processor matches names of the data files to known patterns comprising a client category and a type category.

15. A non-transitory computer readable storage medium configured to store at least one instruction that when executed by a processor causes the processor to perform:
    parsing specified names and specified dates from file names of a plurality of data files stored in a database;
    identifying a defined pattern associated with a particular client and a particular type of data;

identifying a data pattern of each data file of the plurality of data files;

identifying data files, of the plurality of data files, associated with the particular client based on the parsed specified names and the parsed specified dates conforming to the defined pattern associated with the particular client and the particular type of data;

tagging the data files; and transforming content of the data files into a customized data table format associated with requirements of the particular client.

16. The non-transitory computer readable storage medium of claim 15, wherein transforming content of the data files into the customized data table format associated with the known client requirements comprises performing a bulk insert from the plurality of data files into the customized data table format.

17. The non-transitory computer readable storage medium of claim 16, wherein the processor is further configured to perform loading the data files into the database as a binary large object (BLOB).

18. The non-transitory computer readable storage medium of claim 15, further configured to store at least one instructions that causes the processor to perform:

identifying a year and month from the data file names; and logging a status of each of the data files.

19. The non-transitory computer readable storage medium of claim 18, wherein tagging the data files comprises labeling the data files with one or more of a client identifier, a type identifier, year identifier and a month identifier.

20. The non-transitory computer readable storage medium of claim 19, further configured to store at least one instructions that causes the processor to perform:

loading a column or row in a table with content of the tagged data files based on the data file labels; and matching names of the data files to known patterns comprising a client category and a type category.

* * * * *